(12) United States Patent
Zhou

(10) Patent No.: US 11,246,909 B2
(45) Date of Patent: *Feb. 15, 2022

(54) NEUREGULIN BASED METHODS FOR TREATING HEART FAILURE

(71) Applicant: Zensun (Shanghai) Science & Technology, Co., Ltd., Shanghai (CN)

(72) Inventor: Mingdong Zhou, Shanghai (CN)

(73) Assignee: Zensun (Shanghai) Science & Technology, Co., Ltd., Shanghai (CN)

(*) Notice: Subject to any disclaimer, the term of this patent is extended or adjusted under 35 U.S.C. 154(b) by 0 days.

This patent is subject to a terminal disclaimer.

(21) Appl. No.: 15/601,856

(22) Filed: May 22, 2017

(65) Prior Publication Data

US 2018/0104311 A1 Apr. 19, 2018

Related U.S. Application Data

(63) Continuation of application No. 14/746,717, filed on Jun. 22, 2015, now Pat. No. 9,655,949, which is a continuation of application No. 13/376,865, filed as application No. PCT/CN2010/000845 on Jun. 12, 2010, now Pat. No. 9,089,524.

(60) Provisional application No. 61/236,849, filed on Aug. 25, 2009.

(51) Int. Cl.
| | | |
|---|---|---|
| *A61K 38/16* | (2006.01) |
| *A61K 38/18* | (2006.01) |
| *C07K 14/475* | (2006.01) |
| *G06K 9/00* | (2022.01) |
| *H01L 27/20* | (2006.01) |

(52) U.S. Cl.
CPC ...... *A61K 38/1883* (2013.01); *A61K 38/1808* (2013.01); *G06K 9/0002* (2013.01); *H01L 27/20* (2013.01)

(58) Field of Classification Search
None
See application file for complete search history.

(56) References Cited

U.S. PATENT DOCUMENTS

| | | |
|---|---|---|
| 5,530,109 A | 6/1996 | Goodearl et al. |
| 5,716,930 A | 2/1998 | Goodearl et al. |
| 5,834,229 A | 11/1998 | Vandlen et al. |
| 6,635,249 B1 | 10/2003 | Marchionni et al. |
| 7,226,907 B1 | 6/2007 | Zhou |
| 7,612,164 B2 | 11/2009 | Zhou |
| 7,795,212 B2 | 9/2010 | Zhou |
| 7,964,555 B2 | 6/2011 | Zhou |
| 8,476,405 B2 | 7/2013 | Zhou |
| 8,609,620 B2 | 12/2013 | Zhou |
| 8,785,387 B2 | 7/2014 | Zhou |
| 9,012,400 B2 | 4/2015 | Zhou |
| 9,089,524 B2 | 7/2015 | Zhou |
| 9,340,597 B2 | 5/2016 | Zhou |
| 9,434,777 B2 | 9/2016 | Zhou |
| 9,555,076 B2 | 1/2017 | Zhou |
| 9,580,515 B2 | 2/2017 | Zhou |
| 9,655,949 B2 | 5/2017 | Zhou |
| 10,098,834 B2 | 10/2018 | Zhou |
| 10,112,983 B2 | 10/2018 | Zhou |
| 10,227,418 B2 | 3/2019 | Zhou |
| 10,441,633 B2 | 10/2019 | Zhou |
| 10,561,709 B2 | 2/2020 | Zhou |
| 10,702,585 B2 | 7/2020 | Zhou |
| 2006/0194734 A1 | 8/2006 | Zhou |
| 2007/0129296 A1 | 6/2007 | Zhou |
| 2007/0190127 A1 | 8/2007 | Zhou |
| 2007/0213264 A1 | 9/2007 | Zhou |
| 2009/0156488 A1 | 6/2009 | Zhou |
| 2011/0229444 A1 | 9/2011 | Zhou |
| 2013/0078235 A1 | 3/2013 | Zhou |
| 2014/0031284 A1 | 1/2014 | Zhou |
| 2014/0135265 A1 | 5/2014 | Zhou |
| 2016/0089329 A1 | 3/2016 | Zhou |
| 2016/0095903 A1 | 4/2016 | Zhou |
| 2016/0297859 A1 | 10/2016 | Zhou |
| 2017/0007671 A1 | 1/2017 | Zhou |
| 2017/0232068 A1 | 8/2017 | Zhou |
| 2017/0313784 A1 | 11/2017 | Zhou |
| 2017/0360889 A1 | 12/2017 | Zhou |
| 2017/0368140 A1 | 12/2017 | Zhou |

FOREIGN PATENT DOCUMENTS

| | | |
|---|---|---|
| CN | 1276381 A | 12/2000 |
| CN | 101394861 A | 3/2009 |
| WO | WO 97/09425 A1 | 3/1997 |
| WO | WO 00/37095 A1 | 6/2000 |
| WO | WO 00/64400 A2 | 11/2000 |
| WO | WO 03/099300 A1 | 12/2003 |
| WO | WO 03/099320 A1 | 12/2003 |
| WO | WO 03/099321 A1 | 12/2003 |
| WO | WO 2007/062594 A1 | 6/2007 |

(Continued)

OTHER PUBLICATIONS

Carraway et al., "Neuregulin-2, a new ligand of ErbB3/ErbB4-receptor tyrosine kinases," Nature, 387:512-516 (1997).

Chang et al., "Ligands for ErbB-family receptors encoded by a neuregulin-like gene," Nature, 387:509-512 (1997).

Higashiyama et al., "A novel brain-derived member of the epidermal growth factor family that interacts with ErbB3 and ErbB4," J. Biochem., 122:675-680 (1997).

(Continued)

*Primary Examiner* — Christine J Saoud
*Assistant Examiner* — Jon M Lockard
(74) *Attorney, Agent, or Firm* — Jones Day

(57) ABSTRACT

The present invention features methods of treating patients with chronic heart failure by administering a neuregulin polypeptide within a dosage range which is both effective and safe.

12 Claims, No Drawings

Specification includes a Sequence Listing.

(56) References Cited

FOREIGN PATENT DOCUMENTS

| | | |
|---|---|---|
| WO | WO 2007/076701 A1 | 7/2007 |
| WO | WO 2008/028405 A1 | 3/2008 |
| WO | WO 2009/033373 A1 | 3/2009 |
| WO | WO 2010/060265 A1 | 6/2010 |
| WO | WO 2010/060266 A1 | 6/2010 |
| WO | WO 2010/142141 A1 | 12/2010 |
| WO | WO 2011/091723 | 8/2011 |
| WO | WO 2013/053076 A1 | 4/2013 |
| WO | WO 2013/053158 A1 | 4/2013 |
| WO | WO 2014/187342 A1 | 11/2014 |
| WO | WO 2015/101182 A1 | 7/2015 |
| WO | WO 2016/045493 A1 | 3/2016 |
| WO | WO 2016/058493 A1 | 4/2016 |

OTHER PUBLICATIONS

Hijazi et al., "NRG-3 in human breast cancers: activation of multiple erbB family proteins," Int. J. Oncol., 13:1061-1067 (1998).
Holmes et al., "Identification of heregulin, a specific activator of p185erbB2," Science, 256:1205-1210 (1992).
Liu et al., "Neuregulin-1/erbB-activation improves cardiac function and survival in models of ischemic, dilated, and viral cardiomyoptahy," J. Am. Coll. Cardiol., 48(7):1438-1447 (2006).
Sadick et al., "Analysis of heregulin-induced ErbB2 phosphorylation with a high-throughput Kinase receptor activation enzyme-linked immunosorbant assay," Anal. Biochem., 235:207-214 (1996).
Watson et al., "Molecular Biology of the Gene," 4th Edition, Benjamin-Cummings Publishing Company, p. 224 (1987).

NEUREGULIN BASED METHODS FOR TREATING HEART FAILURE

This application claims the benefit of U.S. patent application Ser. No. 14/746,717 filed Jun. 22, 2015, which claims the benefit of U.S. patent application Ser. No. 13/376,865 filed Jul. 18, 2012, now U.S. Pat. No. 9,089,524, which claims the benefit of PCT/CN2010/000845 filed Jun. 12, 2010 and which claims priority to U.S. Provisional Application No. 61/236,849 filed Aug. 25, 2009, the contents of which are each incorporated herein by reference in their entireties and for all purposes.

1. FIELD OF THE INVENTION

The present invention relates to methods for preventing, treating or delaying heart failure in a mammal using a neuregulin protein. Particularly, the present invention provides the dosage range of neuregulin protein for preventing, treating or delaying heart failure in the mammal.

2. BACKGROUND OF THE INVENTION

Heart failure affects approximately five million Americans, and more than 550,000 new patients are diagnosed with the condition each year. Current drug therapy for heart failure is primarily directed to angiotensin-converting enzyme (ACE) inhibitors, which are vasodilators that cause blood vessels to expand, lowering blood pressure and reducing the heart's workload. While the percent reduction in mortality has been significant, the actual reduction in mortality with ACE inhibitors has averaged only 3%-4%, and there are several potential side effects. Additional limitations are associated with other options for preventing or treating heart failure. For example, heart transplantation is clearly more expensive and invasive than drug treatment, and it is further limited by the availability of donor hearts. Use of mechanical devices, such as biventricular pacemakers, is similarly invasive and expensive. Thus, there has been a need for new therapies given the deficiencies in current therapies.

One promising new therapy involves administration of neuregulin (hereinafter referred to as "NRG") to a patient suffering from or at risk of developing heart failure. NRGs, a family of EGF-like growth factors, comprises a family of structurally related growth and differentiation factors that include NRG1, NRG2, NRG3 and NRG4 and isoforms thereof, are involved in an array of biological responses: stimulation of breast cancer cell differentiation and secretion of milk proteins; induction of neural crest cell differentiation to Schwann cells; stimulation of skeletal muscle cell synthesis of acetylcholine receptors; and, promotion of myocardial cell survival and DNA synthesis. In vivo studies of neuregulin gene-targeted homozygous mouse embryos with severe defects in ventricular trabeculae formation and dorsal root ganglia development indicate that neuregulin is essential for heart and neural development.

NRGs bind to the EGF receptor family, which comprises EGFR, ErbB2, ErbB3 and ErbB4, each of which plays an important role in multiple cellular functions, including cell growth, differentiation and survival. They are protein tyrosine kinase receptors, consisting of an extracellular ligand-binding domain, transmembrane kinase domain and cytoplasmic tyrosine kinase domain. After NRG bind to the extracellular domain of ErbB3 or ErbB4, it induces a conformational change that leads to heterodimer formation between ErbB3, ErbB4 and ErbB2 or homodimer formation between ErbB4 itself, which results in phosphorylation of the receptor's C-terminal domain inside the cell membrane. The phosphorylated intracellular domain then binds additional signal proteins inside the cell, activating the corresponding downstream AKT or ERK signaling pathway, and inducing a series of cell reactions, such as stimulation or depression of cell proliferation, cell differentiation, cell apoptosis, cell migration or cell adhesion. Among these receptors, mainly ErbB2 and ErbB4 are expressed in the heart.

It has been shown that the EGF-like domains of NRG-1, ranging in size from 50 to 64-amino acids, are sufficient to bind to and activate these receptors. Previous studies have shown that neuregulin-1β (NRG-1β) can bind directly to ErbB3 and ErbB4 with high affinity. The orphan receptor, ErbB2, can form heterodimer with ErbB3 and ErbB4 with higher affinity than ErbB3 or ErbB4 homodimers. Research in neural development has indicated that the formation of the sympathetic nervous system requires an intact NRG-1β, ErbB2 and ErbB3 signaling system. Targeted disruption of the NRG-1β or ErbB2 or ErbB4 led to embryonic lethality due to cardiac development defects. Recent studies also highlighted the roles of NRG-1β, ErbB2 and ErbB4 in the cardiovascular development as well as in the maintenance of adult normal heart function. NRG-1β has been shown to enhance sarcomere organization in adult cardiomyocytes. The administration of a recombinant NRG-1β EGF-like domain significantly improves or protects against deterioration in myocardial performance in distinct animal models of heart failure. More importantly, NRG-1β significantly prolongs survival of heart failure animals. These effects make NRG-1β promising as a broad spectrum therapeutic or lead compound for heart failure due to a variety of common diseases. However, there is still a need for more information about the tolerance and effective dosage of NRG, which can be used in a clinical setting for prevention, treating or delaying of heart failure.

3. SUMMARY OF THE INVENTION

The present invention is based on the discovery that NRG enhances cardiac muscle cell differentiation and organization of sarcomeric and cytoskeleton structure, as well as cell adhesion. The present invention is also based on the discovery that NRG significantly improves or protects against deterioration in myocardial performance in distinct animal models of heart failure and prolongs survival of heart failure animals. Neuregulin, neuregulin polypeptide, neuregulin derivatives, or compounds which mimic the activities of neuregulins, fall within the scope of the methods of the present invention.

In a first aspect of the invention, the tolerance dosage range of NRG protein when used in mammals (e.g., humans) is provided. Said tolerance dosage range means the largest quantity of NRG that may be administrated into the mammal (e.g., human) without harm. In one embodiment, the tolerance dosage range does not exceed 2.4 μg/kg/day, e.g., 2.4 μg/kg/day, 1.2 μg/kg/day, 0.6 μg/kg/day or 0.3 μg/kg/day. In one embodiment, the tolerance dosage range does not exceed 48 U/kg/day, e.g., 48 U/kg/day, 24 U/kg/day, 12 U/kg/day or 6 U/kg/day. In another embodiment, the tolerance dosage range does not exceed 0.34 nmol/kg/day, e.g., 0.34 nmol/kg/day, 0.17 nmol/kg/day, 0.08 nmol/kg/day or 0.04 nmol/kg/day.

In a second aspect of the invention, the effective dosage range of NRG protein for preventing, treating or delaying heart failure in mammals (e.g., humans) is provided. Said effective dosage range means the quantity of NRG that will produce one or more beneficial effects when administered into the mammal (e.g., human). The beneficial effects could be improvement of heart function of patients with heart failure, or prevention of the deterioration of heart function of patients with heart failure, or delaying the deterioration of heart function of patients with heart failure. In one embodiment, the effective dosage range is 0.3-2.4 µg/kg/day, e.g., 2.4 µg/kg/day, 1.2 µg/kg/day, 0.6 µg/kg/day or 0.3 µg/kg/day. In one embodiment, the effective dosage range is 6-48 U/kg/day, e.g., 48 U/kg/day, 24 U/kg/day, 12 U/kg/day or 6 U/kg/day. In another embodiment, the effective dosage range is 0.04-0.34 nmol/kg/day, e.g., 0.34 nmol/kg/day, 0.17 nmol/kg/day, 0.08 nmol/kg/day or 0.04 nmol/kg/day.

In a third aspect of the invention, a method is provided for preventing, treating or delaying heart failure in mammals (e.g., humans), the method comprising administrating a NRG protein within the tolerance dosage range into the mammal (e.g., human) in need thereof. In one embodiment, the NRG protein within the tolerance dosage range is administered once a day. In another embodiment, the NRG protein within the tolerance dosage range is administered several times per day. In one embodiment, the NRG protein within the tolerance dosage range is administered for one day. In another embodiment, the NRG protein within the tolerance dosage range is administered for several days.

In a fourth aspect of the invention, a method is provided for preventing, treating or delaying heart failure in mammals (e.g., humans), the method comprising administrating a NRG protein within the effective dosage range into the mammal (e.g., human) in need thereof. In one embodiment, the NRG protein within the effective dosage range is administered once a day. In another embodiment, the NRG protein within the effective dosage range is administered several times per day. In one embodiment, the NRG protein within the effective dosage range is administer for one day. In another embodiment, the NRG protein within the effective dosage range is administered for several days.

In a fifth aspect of the invention, a pharmaceutical composition for preventing, treating or delaying heart failure is provided, the composition comprises NRG protein with the amount within the tolerance dosage range.

In a sixth aspect of the invention, a pharmaceutical composition for preventing, treating or delaying heart failure is provided, the composition comprises NRG protein with the amount within the effective dosage range.

In a seventh aspect of the invention, a kit for preventing, treating or delaying heart failure is provided, the kit comprises one dose of or several doses of aforesaid pharmaceutical composition for preventing, treating or delaying heart failure.

4. DETAILED DESCRIPTION OF THE INVENTION

Although any methods similar or equivalent to those described herein can be used in the practice of the present invention, the preferred methods and materials are now described.

The present invention provides methods for preventing, treating or delaying heart failure in mammals (e.g., humans) in need thereof using a NRG protein within the tolerance and/or effective dosage range. Preferably, the mammals (e.g., humans) are subjects or patients suffering from or at risk of developing heart failure.

For clarity of disclosure, and not by way of limitation, the detailed description of the invention hereinafter is divided into the subsections that follow. All publications mentioned herein are incorporated by reference to disclose and describe the methods and/or materials in connection with which the publications are cited.

A. DEFINITIONS

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, the singular forms "a", "an", and "the" mean "at least one" or "one or more" unless the context clearly dictates otherwise.

As used herein, "neuregulin" or "NRG" used in the present invention refers to proteins or peptides that can bind and activate ErbB2, ErbB3, ErbB4 or combinations thereof, including but not limited to all neuregulin isoforms, neuregulin EGF domain alone, polypeptides comprising neuregulin EGF-like domain, neuregulin mutants or derivatives, and any kind of neuregulin-like gene products that also activate the above receptors as described in detail below. Neuregulin also includes NRG-1, NRG-2, NRG-3 and NRG-4 proteins, peptides, fragments and compounds that mimic the activities of neuregulin. Neuregulin used in the present invention can activate the above ErbB receptors and modulate their biological reactions, e.g., stimulate acetylcholine receptor synthesis in skeletal muscle cell; and/or improve cardiocyte differentiation, survival and DNA synthesis. Neuregulin also includes those variants with conservative amino acid substitutions that do not substantially alter their biological activity. Suitable conservative substitutions of amino acids are known to those of skill in this art and may be made generally without altering the biological activity of the resulting molecule. Those of skill in this art recognize that, in general, single amino acid substitutions in nonessential regions of a polypeptide do not substantially alter biological activity (see, e.g., Watson et al., Molecular Biology of the Gene, $4^{th}$ Edition, 1987, The Bejacmin/Cummings Pub.co., p. 224). In preferred embodiments, neuregulin used in the present invention binds to and activates ErbB2/ErbB4 or ErbB2/ErbB3 heterodimers, for example, but not for the purpose of restriction, peptides including the 177-237 residues of NRG-1 β2 isoform containing the amino acid sequence: SHLVKCAEKEKTFCVNGGECFMVKDLSNPSRYLCKC PNEFTGDRCQNYVMASFYKAEELYQ (SEQ ID NO:1).

Neuregulin can be administered by any route according to the judgment of those skill in the art, including but not limited to orally, inhalationally, parenterally (e.g., intravenously, intramuscularly, subcutaneously, or intradermally). In certain embodiments, neuregulin is administered orally. In certain embodiments, neuregulin is administered intravenously. In certain embodiments, neuregulin is administered subcutaneously. In preferred embodiments, neuregulin is extendedly released to the mammal intravenously or subcutaneously.

Extended release of neuregulin provides continuous therapeutic level of neuregulin over a period of time. In some embodiments, neuregulin is released over a period of 1 hour, 2 hours, 4 hours, 8 hours, 10 hours, 12 hours, 14 hours, 16 hours, 20 hours, 24 hours or longer. In some embodiments, neuregulin is released over a period of 1 day, 2 days, 3 days, 4 days, 5 days, 6 days, 7 days, 8 days, 9 days, 10 days or longer. In another embodiments, neuregulin is released over a period of 1 week, 2 weeks, 3 weeks, 4 weeks or longer. In another embodiments, neuregulin is released over a period of 1 month, 2 months, 4 months, 8 months, 12 months or longer. In another embodiments, neuregulin is released over a period of 1 year, 2 years, 3 years, 4 years or longer. In another embodiments, neuregulin is released 4 hours each day for consecutive 3 days, 4 hours each day for consecutive 5 days, 4 hours each day for consecutive 7 days, 4 hours each day for consecutive 10 days, 6 hours each day for consecutive 3 days, 6 hours each day for consecutive 5 days, 6 hours each day for consecutive 7 days, 6 hours each day for consecutive 10 days, 8 hours each day for consecutive 3 days, 8 hours each day for consecutive 5 days, 8 hours each day for consecutive 7 days, 8 hours each day for consecutive 10 days.

As used herein, "epidermal growth factor-like domain" or "EGF-like domain" refers to a polypeptide motif encoded by the neuregulin gene that binds to and activates ErbB2, ErbB3, ErbB4, or combinations thereof, and bears a structural similarity to the EGF receptor-binding domain as disclosed in WO 00/64400, Holmes et al., Science, 256: 1205-1210 (1992); U.S. Pat. Nos. 5,530,109 and 5,716,930; Hijazi et al., Int. J. Oncol., 13:1061-1067 (1998); Chang et al., Nature, 387:509-512 (1997); Carraway et al., Nature, 387:512-516 (1997); Higashiyama et al., J. Biochem., 122: 675-680 (1997); and WO 97/09425, the contents of which are all incorporated herein by reference. In certain embodiments, EGF-like domain binds to and activates ErbB2/ErbB4 or ErbB2/ErbB3 heterodimers. In certain embodiments, EGF-like domain comprises the amino acid sequence of the receptor binding domain of NRG-1. In some embodiments, EGF-like domain comprises the amino acid sequence corresponding to amino acid residues 177-226, 177-237, or 177-240 of NRG-1. In certain embodiments, EGF-like domain comprises the amino acid sequence of the receptor binding domain of NRG-2. In certain embodiments, EGF-like domain comprises the amino acid sequence of the receptor binding domain of NRG-3. In certain embodiments, EGF-like domain comprises the amino acid sequence of the receptor binding domain of NRG-4. In certain embodiments, EGF-like domain comprises the amino acid sequence of Ala Glu Lys Glu Lys Thr Phe Cys Val Asn Gly Gly Glu Cys Phe Met Val Lys Asp Leu Ser Asn Pro (SEQ ID NO:2), as described in U.S. Pat. No. 5,834,229.

As used herein, "tolerance dosage" refers to the largest quantity of NRG that may be administered into a mammal without harm. In certain embodiments, the harm may be determined by the incidence and severity of clinical adverse events, abnormalities of vital signs including blood pressure, heart rate, breath and body temperature, new electrocardiographic changes and physical or laboratory abnormalities. In certain embodiments, tolerance dosage refers to the largest quantity of NRG that may be administered into a human without serious adverse events. In one specific embodiment, the serious adverse events is fatal or life threatening. In another specific embodiment, the serious adverse events results in in-patient hospitalisation or prolonged existing hospitalisation. In another specific embodiment, the serious adverse events results in a persistent or significant disablity or incapacity. In another specific embodiment, the serious adverse events results in myocardial infarction, progression to unstable angina or other increase in myocardial ischaemia. In another specific embodiment, the serious adverse events results in the occurrence of a new sustained arrhythmia, e.g., atrial flutter or fibrillation, ventricular tachycardia or fibrillation, complete heart block. In another specific embodiment, the serious adverse events results in congenital anomaly. In other embodiments, the serious adverse events may not be immediately life threatening or result in death or hospitalisation but may jeopardise the subject or require intervention to prevent one of the outcomes listed above.

As used herein, "effective dosage" refers to the quantity of NRG that will produce one or more beneficial effects when administered into a mammal. In certain embodiments, the beneficial effects may be determined by changes of cardiac function including but not limited by LVEF, LVEDV and LVESV measured by MRI. In certain embodiments, the beneficial effects may be determined by the acute haemodynamics changes, including but not limited by cardiac output, left and right heart filling pressures, pulmonary and systemic blood pressures, and systemic and pulmonary vascular resistance. In certain embodiments, the beneficial effects may be determined by Neuro-hormonal and immunological markers in blood, e.g., noradrenaline, aldosterone, endothelin-1, NT-proBNP, terminal propeptide of type III procollagen (PIIINP), hsCRP, TNF and IL6. In certain embodiments, the beneficial effects may be determined by Six-minute Walk Test. In certain embodiments, the beneficial effects may be determined by New York Heart Association Classification of CHF patients. In certain embodiments, the beneficial effects may be determined by the quality of life (QOL, Minnesota, 1986). In certain embodiments, the beneficial effects may be determined by the frequency of re-hospitalization of the patient. In certain embodiments, the beneficial effects may be determined by the survival rate or mortality of the patients.

As used herein, "treat", "treatment" and "treating" refer to any manner in which the symptoms of a condition, disorder or disease are ameliorated or otherwise beneficially altered. The effect may be prophylactic in terms of completely or partially preventing a disease or symptom thereof and/or may be therapeutic in terms of a partial or complete cure for a disease and/or adverse effect attributable to the disease. Treatment also encompasses any pharmaceutical use of the compositions herein.

As used herein, "left ventricle ejection fraction" or "LVEF" means the portion of blood that is pumped out of a filled ventricle as the result of a heartbeat. It may be defined by the following formula: (LVEDV-LVESV)/LVEDV.

As used herein, "LVEDV" means left ventricular end-diastolic volume.

As used herein, "LVESV" means left ventricular end-systolic volume.

As used herein, "fractional shortening" or "FS" means a ratio of the change in the diameter of the left ventricle between the contracted and relaxed states. It may be defined by the following formula: (LV end diastolic diameter-LV end systolic diameter)/LV end diastolic diameter.

As used herein, "heart failure" means an abnormality of cardiac function where the heart does not pump blood at the rate needed for the requirements of metabolizing tissues. Heart failure includes a wide range of disease states such as congestive heart failure, myocardial infarction, tachyarrhythmia, familial hypertrophic cardiomyopathy, ischemic heart disease, idiopathic dilated cardiomyopathy, myocarditis and the like. The heart failure can be caused by any number of factors, including, without limitation, ischemic, congenital, rheumatic, viral, toxic or idiopathic forms.

Chronic cardiac hypertrophy is a significantly diseased state which is a precursor to congestive heart failure and cardiac arrest.

As used herein, "protein" is synonymous with "polypeptide" or "peptide" unless the context clearly dictates otherwise.

As used herein, "activity unit" or "EU" or "U" means the quantity of standard product that can induce 50% maximal reaction. In other words, to determine the activity unit for a given active agent, the EC50 must be measured. For example, if the EC50 for a batch of product was 0.1 μg, then that would be one unit. Further, if of that products is being used, then 10 EU (1/0.1) is being used. The EC50 can be determined by any method known in the art, including the method employed by the inventor. This determination of the activity unit is important for quality control of genetically engineered products and clinically used drugs, permits product from different pharmaceuticals and/or different batch numbers to be quantified with uniform criteria.

The following is an exemplary, rapid, sensitive, high flux and quantitative method for determination of biological activity of NRG-1 through combining NRG with cell surface ErbB3/ErbB4 molecule and indirect mediation of ErbB2 phosphorylation (See e.g., Michael D. Sadick et al., 1996, Analytical Biochemistry, 235:207-214 and WO03/099300).

Briefly, the assay, termed a kinase receptor activation enzyme-linked immunosorbant assay (KIRA-ELISA), consists of two separate microtiter plates, one for cell culture, ligand stimulation, and cell lysis/receptor solubilization and the other plate for receptor capture and phosphotyrosine ELISA. The assay was developed for analysis of NRG-induced ErbB2 activation and utilizes the stimulation of intact receptor on the adherent breast carcinoma cell line, MCF-7. Membrane proteins are solubilized via Triton X-100 lysis and the receptor is captured in ELISA wells coated with ErbB2-specific antibodies with no cross-reaction to ErbB3 or ErbB4. The degree of receptor phosphorylation is then quantified by antiphosphotyrosine ELISA. A reproducible standard curve is generated with a EC50 of approximately 360 pM for heregulin beta 1 (177-244). When identical samples of HRG beta 1 (177-244) are analyzed by both the KIRA-ELISA and quantitative antiphosphotyrosine Western Blot analysis, the results correlate very closely with one another. The assay described in this report is able to specifically quantify tyrosine phosphorylation of ErbB2 that results from the interaction of HRG with ErbB3 and/or ErbB4.

Since most of the genetically engineered medicines are proteins and polypeptides, their activity can be determined by their amino acid sequences or the activity center formed by their spatial structure. Activity titer of protein and polypeptide is not consistent with their absolute quality, therefore cannot be determined with weight unit as that of chemical drugs. However, biological activity of genetically engineered medicines is generally consistent with their pharmacodynamics and titer determination system established through given biological activity can determine its titer unit. Therefore, biological activity determination can be part of a process of titering the substance with biological activity and is an important component of quality control of genetically engineered product. It is important to determine biological activity criteria for quality control of genetically engineered product and clinically used drugs.

Quantity of standard product that can induce 50% maximal reaction is defined as an activity unit (1 EU). Accordingly, product from different pharmaceuticals and of different batch numbers can be quantitated with uniform criteria.

B. EXAMPLES

The invention is illustrated by the following examples which are not intended to be limiting in any way.

Example 1: A Phase I, Open-Label, Non-Comparative, Single-Dose Study to Evaluate the Tolerance of Recombinant Human Neuregulin-1 for Injection in Healthy Volunteers To determine the safety and tolerance of single dose of recombinant human Neuregulin-1 for injection in healthy subjects, the phase I clinical trial (Protocol ID: KW-70112) was carried out in Peking University First Hospital in China, 28 healthy volunteers were enrolled and were randomized into six dosage groups according to their enrolment order, among which the gender ratio was about 1:1.

Investigational Product:

Specification: Neucardin™, a 61-amino acid polypeptide comprising the EGF-like domain of Neuregulin-1 β2 isoform and having the amino acid sequence set forth in SEQ ID NO:1, with the molecular weight of 7054 Dal (1 μg=0.14 nmol). 250 μg (5000 EU)/vial (1 μg=20 EU).

Preparation: For injection.

Mode of administration: Slow bolus (20 ml/10 min, infusion pump control).

Storage: in safe place, with limited access and protected from light, at 3-8° C.

Dosage Groups:

Twenty eight volunteers were divided into six groups with escalating doses equivalent to 0.2 μg, 0.4 μg, 0.8 μg, 1.2 μg, 1.6 μg and 2.4 μg (refer to Table 1 for details). Started from 0.2 μg/kg, under precondition of confirmation of the safety and tolerability of the former dosage group, the study escalated to next dose.

TABLE 1

Dosage groups and subjects in each group

| Group | Dosage | Samples |
|---|---|---|
| A | 0.2 μg/kg (4 EU/kg) | 4 |
| B | 0.4 μg/kg (8 EU/kg) | 4 |
| C | 0.8 μg/kg (16 EU/kg) | 4 |
| D | 1.2 μg/kg (24 EU/kg) | 5 |
| E | 1.6 μg/kg (32 EU/kg) | 6 |
| F | 2.4 μg/kg (48 EU/kg) | 5 |

Study Procedures

1) Screening period:

Obtain the written informed consent form;

Verify the inclusion/exclusion criteria;

Demographics

Collect the medical history;

Physical examination;

Vital signs (supine blood pressure, pulse, respiratory rate, temperature);

Haematology, urinalysis;

Blood biochemistry;

Serum cardiac markers;

ECG;

Ultrasonic cardiogram;

Blood coagulation test: APTT, PT;

Serology test (including HBsAg, Anti-HCV, Anti-HIV assay);

Chest X-ray;

Urine HCG test (female subject, if necessary);

Record adverse event and serious adverse event;
Record concomitant medications.

2) Baseline: The time from the night before scheduled study drug administration to initiation of study drug administration.
Physical examination;
Vital signs (supine blood pressure, pulse, respiratory rate, temperature);
Specific antibody assay;
Re-verify the inclusion/exclusion criteria;
Record adverse event and serious adverse event;
Record concomitant medication.

3) The day study drug was administrated
Study drug administration;
ECG;
Echocardiography;
Record adverse event and serious adverse event;
Record concomitant medication (each day).

4) The 1st day and 7th day after cessation of drug administration
Physical examination;
Vital signs (supine blood pressure, pulse, respiratory rate, temperature);
Specific antibody assay;
Haematology, urinalysis;
Blood biochemistry;
Serum cardiac markers;
ECG;
Ultrasonic cardiogram (7th day after cessation of drug administration);
Blood coagulation test: APTT, PT;
Urine HCG test (female subject, if necessary);
Record adverse events and serious adverse events;
Record concomitant medications.

5) The 10th day after cessation of drug administration
As to any abnormal item in the 7th day test results after cessation of drug administration, this item was re-tested on the 10th days after dose. After that, it was re-tested with a certain interval until the result became normal.

Results and Analysis

Totally 28 healthy subjects were enrolled into 6 dosage groups of 0.2, 0.4, 0.8, 1.2, 1.6, 2.4 µg/kg, the number of subjects who completed study in each dosage groups was 4, 4, 4, 5, 6, 5 respectively (refer to Table 1).

Adverse events (AE) were monitored from the time informed consent was signed until the end-of-treatment visit. Sixteen subjects (57.1%) experienced at least one adverse event during the course of the study, all adverse events were mild. None of subject experienced moderate or severe adverse events during the study.

During the study, the most frequently reported adverse events were listed in Table 2, adverse events by severity were listed in Table 3.

TABLE 2

Listing of adverse events

| Group | Subject | AE | Severity | Outcome |
|---|---|---|---|---|
| 0.2 µg/kg | 402 | Abnormal ECG | Mild | Recovery |
| 0.8 µg/kg | 101 | Nausea | Mild | Recovery |
| | 102 | Nausea; Lower limb fatigue | Mild | Recovery |
| | 103 | Nausea; Fatigue; Loose stolls; Light headness | Mild | Recovery |
| | 104 | Nausea | Mild | Recovery |
| 1.2 µg/kg | 601 | Abnormal ECG | Mild | Recovery |
| | 603 | Hematology abnormality | Mild | Recovery |
| | 605 | Abnormal ECG | Mild | Recovery |
| 1.6 µg/kg | 201 | Poor appetite; Hematology abnormality | Mild | Recovery |
| | 202 | ECG and Urinary abnormality | Mild | Recovery |
| | 204 | Nausea; Abnormal ECG | Mild | Recovery |
| | 206 | Nausea; Poor appetite | Mild | Recovery |
| 2.4 µg/kg | 302 | Abnormal ECG | Mild | Recovery |
| | 303 | Common cold | Mild | Recovery |
| | 304 | Abnormal ECG | Mild | Recovery |
| | 305 | Nausea; Light headness; Abnormal ECG | Mild | Recovery |

TABLE 3

Summary of adverse events by severity

| | 0.2 µg/kg (N = 4) n (%) | 0.4 µg/kg (N = 4) n (%) | 0.8 µg/kg (N = 4) n (%) | 1.2 µg/kg (N = 5) n (%) | 1.6 µg/kg (N = 6) n (%) | 2.4 µg/kg (N = 5) n (%) | Total (N = 28) n (%) |
|---|---|---|---|---|---|---|---|
| Subjects experienced at least one adverse events | 1 (25.0) | 0 (0.0) | 4 (100.0) | 3 (60.0) | 4 (66.7) | 4 (80.0) | 16 (57.1) |
| Subjects classified by worst adverse events | | | | | | | |
| Mild | 1 (25.0) | 0 (0.0) | 4 (100.0) | 3 (60.0) | 4 (66.7) | 4 (80.0) | 16 (57.1) |
| Moderate | 0 (0.0) | 0 (0.0) | 0 (0.0) | 0 (0.0) | 0 (0.0) | 0 (0.0) | 0 (0.0) |
| Severe | 0 (0.0) | 0 (0.0) | 0 (0.0) | 0 (0.0) | 0 (0.0) | 0 (0.0) | 0 (0.0) |
| Subjects experienced at least one SAE | 0 (0.0) | 0 (0.0) | 0 (0.0) | 0 (0.0) | 0 (0.0) | 0 (0.0) | 0 (0.0) |
| Subjects experienced at least one adverse events leading to premature termination | 0 (0.0) | 0 (0.0) | 0 (0.0) | 0 (0.0) | 0 (0.0) | 0 (0.0) | 0 (0.0) |
| Death | 0 (0.0) | 0 (0.0) | 0 (0.0) | 0 (0.0) | 0 (0.0) | 0 (0.0) | 0 (0.0) |

The study drug related adverse events were ECG abnormality (8 subjects, 28.6%) and gastrointestinal disorders (7 subjects, 25.0%). ECG abnormalities included slight ST-T segment depression, T-wave flattening or minimal T-wave inversion. During study drug administration period and observation period, none of the subjects experienced precordial discomfort, choking sensation, chest pain, dyspnea; blood pressure was normal at 2 hour and 24 hour after dosing; no abnormality was found in blood biochemistry, electrolytes, serum cardiac markers and echocardiography.

All subjects of each dosage were not changed in physical examination parameters from baseline. Serum antibody assay showed negative results in all subjects (refer to Table 4).

TABLE 4

Serum anti-NRG-1 antibody of each group

| Group | First sampling 1:50 | First sampling 1:100 | Second sampling 1:50 | Second sampling 1:100 | Third sampling 1:50 | Third sampling 1:100 |
|---|---|---|---|---|---|---|
| 0.2 µg/kg | 0.18 ± 0.05 | 0.12 ± 0.02 | 0.18 ± 0.06 | 0.13 ± 0.02 | 0.17 ± 0.06 | 0.14 ± 0.02 |
| 0.4 µg/kg | 0.12 ± 0.01 | 0.10 ± 0.01 | 0.12 ± 0.06 | 0.10 ± 0.02 | 0.11 ± 0.01 | 0.10 ± 0.01 |
| 0.8 µg/kg | 0.16 ± 0.05 | 0.15 ± 0.02 | 0.18 ± 0.03 | 0.15 ± 0.04 | 0.18 ± 0.05 | 0.16 ± 0.05 |
| 1.2 µg/kg | 0.12 ± 0.02 | 0.10 ± 0.02 | 0.12 ± 0.03 | 0.10 ± 0.02 | 0.11 ± 0.02 | 0.10 ± 0.02 |
| 1.6 µg/kg | 0.21 ± 0.12 | 0.17 ± 0.08 | 0.22 ± 0.10 | 0.17 ± 0.07 | 0.22 ± 0.10 | 0.18 ± 0.06 |
| 2.4 µg/kg | 0.15 ± 0.04 | 0.15 ± 0.03 | 0.17 ± 0.04 | 0.13 ± 0.03 | 0.14 ± 0.03 | 0.14 ± 0.03 |

The results of the phase I clinical trial showed that in the dosage of not exceeding 2.4 µg/kg/day, the drug-related adverse events are mainly mild ECG abnormality and gastrointestinal disorders, no moderate or severe adverse events were observed. So, dosage not exceeding 2.4 µg/kg/day when administered with a single dose is tolerable.

Example 2: A Phase I, Open-Label, Non-Comparative, Multi-Dose Study to Evaluate the Tolerance of Recombinant Human Neuregulin-1 for Injection in Healthy Volunteers To evaluate the safety and tolerance of multi-dose of recombinant human Neuregulin-1 for injection in healthy subjects for 5 consecutive days, the phase I clinical trial (Protocol ID: KW-70112) was carried out in Peking University First Hospital in China, 32 healthy volunteers were enrolled and were randomized into 4 dosage groups.

Investigational Product:

Specification: Neucardin™, a 61-amino acid polypeptide comprising the EGF-like domain of Neuregulin-1 β2 isoform and having the amino acid sequence set forth in SEQ ID NO:1, with the molecular weight of 7054 Dal (1 µg=0.14 nmol). 250 µg (5000 EU)/vial (1 µg=20 EU).

Preparation: For injection.

Mode of administration: Slow bolus (20 ml/10 min, infusion pump control).

Storage: in safe place, with limited access and protected from light, at 3-8° C.

Dosage Groups:

Thirty two volunteers were divided into four groups with escalating doses equivalent to 0.2 µg, 0.4 µg, 0.8 µg and 1.2 µg (refer to Table 5 for details). Started from 0.2 µg/kg, under precondition of confirmation of the safety and tolerability of the former dosage group, the study escalated to next dose.

TABLE 5

Dosage groups and subjects in each group

| Group | Dosage | Samples |
|---|---|---|
| I (5 days) | 0.2 µg/kg (4EU) | 8 |
| II (5 days) | 0.4 µg/kg (8EU) | 8 |
| III (5 days) | 0.8 µg/kg (16EU) | 8 |
| IV (5 days) | 1.2 µg/kg (24EU) | 8 |

Study Procedures
1) Screening period:
Obtain the written informed consent form;
Verify the inclusion/exclusion criteria;
Demographics;
Collect the medical history;
Physical examination;
Vital signs (supine blood pressure, pulse, respiratory rate, temperature);
Haematology, urinalysis;
Blood biochemistry;
Serum cardiac markers;
ECG;
Ultrasonic cardiogram;
Blood coagulation test: APTT, PT;
Serology test (including HBsAg, Anti-HCV, Anti-HIV assay);
Chest X-ray;
Urine HCG test (female subject, if necessary);
Record adverse event and serious adverse event;
Record concomitant medications.
2) Baseline: The time from the night before scheduled study drug administration to initiation of study drug administration.
Physical examination;
Vital signs (supine blood pressure, pulse, respiratory rate, temperature);
Re-verify the inclusion/exclusion criteria;
Record adverse event and serious adverse event;
Record concomitant medication.
3) 1$^{st}$ day to 5$^{th}$ day of drug administration
Study drug administration;
ECG;
Record adverse event and serious adverse event (each day);
Record concomitant medication (each day).
4) The 1st day and 7th day after cessation of drug administration
Physical examination;
Vital signs (supine blood pressure, pulse, respiratory rate, temperature);
Haematology, urinalysis;

Blood biochemistry;
Serum cardiac markers;
ECG;
Ultrasonic cardiogram (7th day after cessation of drug administration);
Blood coagulation test: APTT, PT;
Urine HCG test (female subject, if necessary);
Record adverse events and serious adverse events;
Record concomitant medications.

5) The 14th day after cessation of drug administration

As to any abnormal item in the 7th day test results after cessation of drug administration, this item was re-tested on the 10th days after dose. After that, it was re-tested with a certain interval until the result became normal.

Results and Analysis

A total of 32 healthy subjects were enrolled and randomized into 4 different dosage groups of 0.2, 0.4, 0.8 and 1.2 µg/kg, with 8 subjects in each group and the gender ratio of 1:1. One subject in 1.2 µg/kg dosage group discontinued the study because of adverse event, all other subjects completed the study.

Adverse events were monitored from the time informed consent was signed until the end-of-treatment visit. Twenty-three subjects (71.9%) experienced at least one adverse event during the course of the study, all adverse events were mild. None of subject experienced severe or serious adverse events during the study (refer to Table 6).

TABLE 6

| | 0.2 µg/kg (N = 8) n (%) | 0.4 µg/kg (N = 8) n (%) | 0.8 µg/kg (N = 8) n (%) | 1.2 µg/kg (N = 8) n (%) | Total (N = 32) n (%) |
|---|---|---|---|---|---|
| Adverse events by severity | | | | | |
| Subjects experienced at least one adverse events | 4 (50.0) | 5 (62.5) | 7 (87.5) | 7 (87.5) | 23 (71.9) |
| Subjects classified by worst adverse events | | | | | |
| Mild | 4 (50.0) | 5 (62.5) | 7 (87.5) | 7 (87.5) | 23 (71.9) |
| Moderate | 0 (0.0) | 0 (0.0) | 0 (0.0) | 0 (0.0) | 0 (0.0) |
| Severe | 0 (0.0) | 0 (0.0) | 0 (0.0) | 0 (0.0) | 0 (0.0) |
| Subjects experienced at least one SAE | 0 (0.0) | 0 (0.0) | 0 (0.0) | 0 (0.0) | 0 (0.0) |
| Subjects experienced at least one adverse events leading to premature termination | 0 (0.0) | 0 (0.0) | 0 (0.0) | 1 (12.5) | 1 (3.1) |
| Death | 0 (0.0) | 0 (0.0) | 0 (0.0) | 0 (0.0) | 0 (0.0) |

The frequently reported study drug related adverse events included ECG abnormalities (14 cases, 40.63%) and gastrointestinal disorders (9 cases, 28.13%). ECG abnormalities included slight STT segment depression, T-wave flattening or minimal T-wave inversion. During study drug administration period and observation period, none of the subjects with abnormal ECG experienced precordial discomfort, choking sensation, chest pain, and dyspnea. No treatment was taken in the whole process of study, almost all ECG abnormalities return to normal within 48 hours after $5^{th}$ study drug administration.

Gastrointestinal disorders related to study drug were stomach discomfort, nausea, vomit and loose stools (refer to Table 7).

TABLE 7

| MedDRA system organ class/ MedDRA preferred term | 0.2 µg/kg (N = 8) n (%) | 0.4 µg/kg (N = 8) n (%) | 0.8 µg/kg (N = 8) n (%) | 1.2 µg/kg (N = 8) n (%) | Total (N = 32) n (%) |
|---|---|---|---|---|---|
| Frequently reported study drug related adverse events | | | | | |
| Subjects experienced at least one adverse event | 2 (25.0) | 4 (50.0) | 7 (87.5) | 7 (87.5) | 20 (62.5) |
| Skin and hypodermis disorders | 0 (0.0) | 0 (0.0) | 2 (25.0) | 0 (0.0) | 2 (6.3) |
| Rash | 0 (0.0) | 0 (0.0) | 2 (25.0) | 0 (0.0) | 2 (6.3) |
| Nervous system disorder | 0 (0.0) | 0 (0.0) | 1 (12.5) | 0 (0.0) | 1 (3.1) |
| Headache | 0 (0.0) | 0 (0.0) | 1 (12.5) | 0 (0.0) | 1 (3.1) |
| Gastrointestinal disorder | 0 (0.0) | 1 (12.5) | 4 (50.0) | 4 (50.0) | 9 (28.1) |
| Nausea | 0 (0.0) | 0 (0.0) | 4 (50.0) | 2 (25.0) | 6 (18.8) |
| Vomit | 0 (0.0) | 0 (0.0) | 0 (0.0) | 2 (25.0) | 2 (6.3) |
| Stomach discomfort | 0 (0.0) | 1 (12.5) | 0 (0.0) | 0 (0.0) | 1 (3.1) |
| Loose stool | 0 (0.0) | 0 (0.0) | 0 (0.0) | 1 (12.5) | 1 (3.1) |
| Cardiac disorder | 2 (25.0) | 0 (0.0) | 0 (0.0) | 0 (0.0) | 2 (6.3) |
| Ventricular arrhythmia | 2 (25.0) | 0 (0.0) | 0 (0.0) | 0 (0.0) | 2 (6.3) |
| ECG abnormalities | 0 (0.0) | 3 (37.5) | 5 (62.5) | 6 (75.0) | 14 (43.8) |
| T wave inversion | 0 (0.0) | 2 (25.0) | 2 (25.0) | 3 (37.5) | 7 (21.9) |
| T wave depression | 0 (0.0) | 2 (25.0) | 5 (62.5) | 4 (50.0) | 11 (34.4) |
| T wave abnormalities | 0 (0.0) | 0 (0.0) | 0 (0.0) | 1 (12.5) | 1 (3.1) |

The results of the phase I clinical trial showed that in the dosage of not exceeding 1.2 μg/kg/day, the drug-related adverse events are mainly mild ECG abnormality and gastrointestinal disorders, no moderate or severe adverse events were observed. The AEs experienced in this multi-dose trial were similar with that of single-dose trial, supporting that the incidence and intensity of AEs will not increase when the study drug was administered for multiple days.

Example 3: An Open-Label, Single-Center, Parallel Group Study to Evaluate the Efficacy and Safety of Recombinant Human Neuregulin-1 for Injection in Heart Failure Patients on Standard Therapy To evaluate the efficacy and safety of recombinant human neuregulin-1 for injection on chronic heart failure and to investigate the effective dosage range of recombinant human neuregulin-1 for injection for treating chronic heart failure, the phase II, open-label, single-center, parallel group, standard treatment based study (Protocol ID: HREC 06/035) was carried out in St Vincent's Hospital in Australia. Fifteen patients with chronic heart failure were enrolled and randomized into 3 groups.

Investigational Product:
Specification: Neucardin™, a 61-amino acid polypeptide comprising the EGF-like domain of Neuregulin-1 β2 isoform and having the amino acid sequence set forth in SEQ ID NO:1, with the molecular weight of 7054 Dal (1 μg=0.14 nmol). 250 μg (5000 EU)/vial (1 μg=20 EU).

Preparation: For injection.
Mode of administration: Intravenously drip.
Storage: in safe place, with limited access and protected from light, at 3-8° C.

Dosage Groups:
Fifteen patients with chronic heart failure (LVEF≤40%, NYHA class established on ACEI/ARA and beta blocker with stable doses of these medications for the preceding 3 months) were enrolled and randomized into 3 dosage groups with 5 patients in each group (refer to Table 8).

TABLE 8

Dosage regimen of phase II trial in Australia

| Dosage group | Sample | Dosage ($1^{st}$ day) | Dosage ($2^{nd}$-$11^{th}$ day) |
|---|---|---|---|
| A | 5 | 1.2 μg/kg/6 hrs | 2.4 μg/kg/12 hrs |
| B | 5 | 1.2 μg/kg/6 hrs | 1.2 μg/kg/12 hrs |
| C | 5 | 1.2 μg/kg/6 hrs | 0.6 μg/kg/12 hrs |

Study Procedures
1) Screening and baseline:
Obtain the written informed consent form;
Collect the medical history;
Vital signs (supine blood pressure, pulse, respiratory rate, temperature);
Physical examination;
Verify the inclusion/exclusion criteria;
ECG;
FBC;
Neurohormonal, immunological marker (NT-proBNP、PIIINP、NA、Aldos、Endothelin、hsCRP、TNF-α、IL-6);
Ultrasonic cardiogram;
MRI.

2) $1^{st}$ day of drug administration
Vital signs (supine blood pressure, pulse, respiratory rate, temperature);
Study drug administration;
ECG;
RH Catheter;
NT-proBNP.

3) $2^{nd}$ to $11^{th}$ day of drug administration
Vital signs (supine blood pressure, pulse, respiratory rate, temperature);
Study drug administration;
ECG 4) $12^{th}$ day of the study
Vital signs (supine blood pressure, pulse, respiratory rate, temperature);
ECG;
RH Catheter;
FBC;
Neurohormonal, immunological marker (NT-proBNP、PIIINP、NA、Aldos、Endothelin、hsCRP、TNF-α、IL-6);
Ultrasonic cardiogram;
MRI.

5) $30^{th}$ day of the study
Vital signs (supine blood pressure, pulse, respiratory rate, temperature);
ECG;
FBC;
Neurohormonal, immunological marker (NT-proBNP、PIIINP、NA、Aldos、Endothelin、hsCRP、TNF-α、IL-6);
Ultrasonic cardiogram;
MRI.

6) $60^{th}$ day of the study
Vital signs (supine blood pressure, pulse, respiratory rate, temperature);
ECG;
FBC;
Neurohormonal, immunological marker (NT-proBNP、PIIINP、NA、Aldos、Endothelin、hsCRP、TNF-α、IL-6);

7) $90^{th}$ day of the study
Collect the medical history;
Vital signs (supine blood pressure, pulse, respiratory rate, temperature);
Physical examination;
ECG;
FBC;
RH Catheter;
Neurohormonal, immunological marker (NT-proBNP、PIIINP、NA、Aldos、Endothelin、hsCRP、TNF-α、IL-6);
Ultrasonic cardiogram;
MRI.

Results and Analysis
The primary efficacy endpoint is evaluating the left ventricular function and remodeling (as determined by change in LVEF, LVEDV and LVESV measured by MRI). Hemodynamics parameters and neurohormonal and immunological markers act as secondary efficacy endpoints.

As a total count, 13 subjects (13/15, 86.7%) received the test drug by IV infusion for 11 consecutive days, one subject (1/15, 6.7%) received the test drug by IV infusion for 10 days, one subject (1/15, 6.7%) received the test drug by IV infusion for 7 days. No subject withdrew.

In Group A (1.2 μg/kg/day*1 day+2.4 μg/kg/day*10 days), 4 subjects (4/5, 80.0%) received the test drug by IV infusion for 11 consecutive days, one subject (1/5, 20.0%) received the test drug by IV infusion for 7 days. In Group B (1.2 μg/kg/day*1 day+1.2 μg/kg/day*10 days), 5 subjects (5/5, 100.0%) received the test drug by IV infusion for 11 consecutive days. In Group C (1.2 μg/kg/day*1 day+0.6 μg/kg/day*10 days), 4 subjects (4/5, 80.0%) received the test drug by IV infusion for 11 consecutive days, one subject (1/5, 20%) received the test drug by IV infusion for 10 days.

In group A, after the administration of Neucardin™, at Day 12, the LVEF (%) was improved by 5.4% compared to baseline; the percentage increase was 16.0%; at 1 Month, the LVEF (%) was improved by 3.3% compared to baseline, the percentage of increase was 8.8%; at 3 Months, the LVEF (%) was still improved by 2.6% compared to baseline, the percentage of increase was 6.1%.

In group B, at Day 12, the LVEF (%) was improved by 3.8% compared to baseline; the percentage increase was 11.8%; at 1 Month, the LVEF (%) was improved by 3.4% compared to baseline, the percentage of increase was 9.7%; at 3 Months, the improvement of LVEF (%) was increased to 4.8% compared to baseline, the percentage of increase was 15.7%.

In group C, at Day 12, the LVEF (%) was improved by 2.2% compared to baseline; the percentage increase was 8.4%; at 1 Month, the LVEF (%) was improved by 4.6% compared to baseline, the percentage of increase was 15.4%; and the improvement of LVEF (%) sustained to 3 Months by 4.4% compared to baseline, the percentage of increase was 15.5%.

And for all 15 subjects who completed the study (combined), the improvement of LVEF (%) was 3.8%, 3.8% and 3.9% at day 12, 1 month, 3 month, compared to baseline, respectively (refer to Table 9).

For all 15 subjects who completed the study (combined) and for each individual dosage group, there was no significant change compared to baseline in LVEDV (ml) at any time point.

Concerning LVESV (ml), in group A, at Day 12, the LVESV (ml) was decreased by 8.4 ml compared to baseline, the percentage decrease was 4.9%; At 1 Month, the LVESV (ml) was decreased by 14.3 ml compared to baseline, the percentage decrease was 8.8%; At 3 month, the LVESV (ml) was decreased by 12.0 ml compared to baseline, the percentage decrease was 8.3%.

TABLE 9

Measured values (Mean ± SD) of LVEF (%)

| Dosage group | Time points | Measured LVEF value (%) | Absolute change of LVEF (%) | Percent change of LVEF compared to baseline (%) |
|---|---|---|---|---|
| Group A | Baseline (n = 5) | 33.2 ± 9.7 | | |
| (1.2 mcg/kg/day * 1 day + | Day 12 (n = 5) | 38.6 ± 11.6 | 5.4 ± 2.9 | 16.0 ± 8.2 |
| 2.4 mcg/kg/day * 10 days) | 1 Month (n = 4) | 37.5 ± 13.1 | 3.3 ± 2.8 | 8.8 ± 6.3 |
| | 3 Months (n = 5) | 35.8 ± 13.1 | 2.6 ± 4.0 | 6.1 ± 11.0 |
| Group B | Baseline (n = 5) | 30.8 ± 8.0 | | |
| (1.2 mcg/kg/day * 1 day + | Day 12 (n = 5) | 34.6 ± 10.0 | 3.8 ± 2.6 | 11.8 ± 5.9 |
| 1.2 mcg/kg/day * 10 days) | 1 Month (n = 5) | 34.2 ± 10.9 | 3.4 ± 4.1 | 9.7 ± 12.4 |
| | 3 Months (n = 5) | 35.6 ± 9.4 | 4.8 ± 3.4 | 15.7 ± 11.2 |
| Group C | Baseline (n = 5) | 32.6 ± 7.3 | | |
| (1.2 mcg/kg/day * 1 day + | Day 12 (n = 5) | 34.8 ± 5.4 | 2.2 ± 3.7 | 8.4 ± 11.9 |
| 0.6 mcg/kg/day * 10 days) | 1 Month (n = 5) | 37.2 ± 6.8 | 4.6 ± 3.4 | 15.4 ± 11.5 |
| | 3 Months (n = 5) | 37.0 ± 5.2 | 4.4 ± 3.0 | 15.5 ± 12.9 |
| All subjects | Baseline (n = 15) | 32.2 ± 7.9 | | |
| | Day 12 (n = 15) | 36.0 ± 8.9 | 3.8 ± 3.2 | 12.1 ± 8.9 |
| | 1 Month (n = 14) | 36.2 ± 9.6 | 3.8 ± 3.3 | 11.5 ± 10.3 |
| | 3 Months (n = 15) | 36.1 ± 9.1 | 3.9 ± 3.4 | 12.4 ± 11.8 |

In group B, at Day 12, the LVESV (ml) was decreased by 1.0 ml compared to baseline, the percentage decrease was 2.5%; At 1 Month, the LVESV (ml) was decreased by 3.8 ml compared to baseline, the percentage decrease was 2.5%; At 3 month, the LVESV (ml) was decreased by 12.6 ml compared to baseline, the percentage decrease was 6.3%.

In group C, at Day 12, the LVESV (ml) was decreased by 11.4 ml compared to baseline, the percentage decrease was 8.6%; At 1 Month, the LVESV (ml) was decreased by 8.0 ml compared to baseline, the percentage decrease was 5.1%; At 3 month, the LVESV (ml) was decreased by 10.8 ml compared to baseline, the percentage decrease was 7.1%.

And for all 15 subjects who completed the study (combined), the decrease of LVESV (ml) was 6.9, 8.3 and 11.8 ml at day 12, 1 month, 3 month, compared to baseline, respectively (refer to Table 10).

TABLE 10

Measured values (Mean ± SD) of LVESV (ml)

| Dosage groups | Time points | Measured value of LVESV (ml) | Absolutely change of LVESV (ml) | Percent change of LVESV compared to baseline (%) |
|---|---|---|---|---|
| Group A | Baseline (n = 5) | 194.2 ± 74.0 | | |
| (1.2 mcg/kg/day * 1 day + | Day 12 (n = 5) | 185.8 ± 73.2 | −8.4 ± 10.4 | −4.9 ± 6.3 |
| 2.4 mcg/kg/day * 10 days) | 1 Month (n = 4) | 172.8 ± 81.5 | −14.3 ± 14.9 | −8.8 ± 9.8 |
| | 3 Months (n = 5) | 182.2 ± 83.4 | −12.0 ± 17.6 | −8.3 ± 11.4 |
| Group B | Baseline (n = 5) | 179.6 ± 34.7 | | |
| (1.2 mcg/kg/day * 1 day + | Day 12 (n = 5) | 178.6 ± 60.5 | −1.0 ± 29.0 | −2.5 ± 16.6 |
| 1.2 mcg/kg/day * 10 days) | 1 Month (n = 5) | 175.8 ± 40.1 | −3.8 ± 14.5 | −2.5 ± 8.3 |
| | 3 Months (n = 5) | 167.0 ± 26.0 | −12.6 ± 15.6 | −6.3 ± 8.3 |
| Group C | Baseline (n = 5) | 182.4 ± 70.5 | | |
| (1.2 mcg/kg/day * 1 day + | Day 12 (n = 5) | 171.0 ± 81.6 | −11.4 ± 22.2 | −8.6 ± 14.2 |
| 0.6 mcg/kg/day * 10 days) | 1 Month (n = 5) | 174.4 ± 73.4 | −8.0 ± 9.2 | −5.1 ± 6.9 |
| | 3 Months (n = 5) | 171.6 ± 74.4 | −10.8 ± 8.9 | −7.1 ± 6.6 |
| All subjects | Baseline (n = 15) | 185.4 ± 58.1 | | |
| | Day 12 (n = 15) | 178.5 ± 67.2 | −6.9 ± 20.8 | −5.3 ± 12.4 |
| | 1 Month (n = 14) | 174.4 ± 60.7 | −8.3 ± 12.7 | −5.2 ± 8.1 |
| | 3 Months (n = 15) | 173.6 ± 61.7 | −11.8 ± 13.5 | −7.2 ± 8.4 |

A 6-hour infusion of Neucardin™ acutely and significantly influenced several hemodynamic parameters when monitored over 24 hours. As shown in Table 11, the acute influence of Neucardin™ on hemodynamics was quite positive.

TABLE 11

Summary of significant changes in hemodynamics parameters during & after a 6-hour infusion of Neucardin™

| Hemodynamics parameters | Time points when the parameters significantly increased compared to baseline | Time points when the parameters significantly decreased compared to baseline |
|---|---|---|
| Heart rate (HR, beat/min) | 1 Hour, 2 Hours, 4 Hours & 6 Hours | |
| Systolic Blood Pressure (SBP, mmHg) | 6 Hours | |
| Diastolic Blood Pressure (DBP, mmHg) | | 24 Hours |
| Mean Blood Pressure (MBP, mmHg) | | 24 Hours |
| Right Atrial Pressure (RA, mmHg) | | 1 Hour, 2 Hours, 4 Hours, 6 Hours, 12 Hours & 24 Hours |
| Pulmonary Artery Systolic Pressure (PASP, mmHg) | 30 minutes, 1 Hour | |
| Pulmonary Artery Diastolic Pressure (PADP, mmHg) | | 2 Hours, 12 Hours & 24 Hours |
| Mean Pulmonary Arterial Pressure (MPAP, mmHg) | | 2 Hours, 12 Hours & 24 Hours |
| Pulmonary Arterial Wedge Pressure (PAWP, mmHg) | | 30 minutes, 1 Hour, 2 Hours, 4 Hours, 6 Hours, 12 Hours & 24 Hours |
| Transpulmonary Pressure Gradient (TPG, mmHg) | 30 minutes, 1 Hour, 2 Hours, 4 Hours, 6 Hours & 24 Hours | |
| Pulmonary Vascular Resistance (PVR, dynes · sec · cm$^{-5}$) | | |
| Systemic Vascular Resistance (SVR, dynes · sec · cm$^{-5}$) | | 30 minutes, 2 Hours, 4 Hours, 6 Hours & 24 Hours |
| Cardiac Output (CO, L/min) | 30 minutes, 1 Hour, 2 Hours, 4 Hours, 6 Hours & 24 Hours | |
| Cardiac Index (CI, L/min/m$^2$) | 30 minutes, 1 Hour, 2 Hours, 4 Hours, 6 Hours & 24 Hours | |

TABLE 11-continued

Summary of significant changes in hemodynamics parameters during
& after a 6-hour infusion of Neucardin™

| Hemodynamics parameters | Time points when the parameters significantly increased compared to baseline | Time points when the parameters significantly decreased compared to baseline |
|---|---|---|
| Stroke Volume (SV, ml) | 30 minutes, 2 Hours, 4 Hours, 12 Hours & 24 Hours | |
| Stroke Volume Index (SVI, ml/m$^2$) | 30 minutes, 2 Hours, 4 Hours, 12 Hours & 24 Hours | |

The long term significant changes in hemodynamics for the study subjects are summarized in the following table, and details are listed below (Table 12).

TABLE 12

Summary of significant changes in long-term hemodynamic parameters

| Hemodynamics parameters | Time points when the parameters significantly increased compared to baseline | Time points when the parameters significantly decreased compared to baseline |
|---|---|---|
| SBP (mmHg) | Day 12, 3 Months | |
| DBP (mmHg) | Day 12, 3 Months | |
| MBP (mmHg) | Day 12, 3 Months | |
| TPG (mmHg) | Day 12, 3 Months | |
| PAWP (mmHg) | | 3 Months |

Concerning the neurohormonal and immunological biomarkers, the NT-proBNP was increased after the 6-hour infusion of Neucardin™ on the first day, and did not return to baseline at 24 hours from the start of the administration, and after the end of medication, it decreased and returned to baseline at the end of the study.

No significant change was observed in hs-CRP.

Regarding the safety evaluation, 10 subjects (10/15, 66.7%) experienced at least one adverse event (AE). The most commonly reported individual AEs were nausea (20%), lethargy (20%) and chest pain (20%), without a clear causal relationship to dose. Approximately 67% of subjects had ECG abnormalities during or following study drug dosing, including: T wave inversions or flattening, ST-T segment changes, premature ventricular contractions, non-sustained runs of supraventricular or ventricular tachycardia or atrial flutter/fibrillation. As ECG abnormalities are common in CHF subjects and there was no placebo group for comparison, it is difficult to assess causality or relationship to drug in this study.

One subject in Group A (2.4 µg/kg/day) and one subject in Group C (0.6 µg/kg/day) experienced serious adverse event(s) (SAEs).

There were no clinical significant abnormalities identified concerning to vital signs, physical examination, laboratory parameters.

According to the results of the phase II trial, recombinant human neuregulin-1 is believed to be effective and safe to treat patients with chronic heart failure in the dosage range between 0.6 to 2.4 µg/kg/day (12-48 EU/kg/day or 0.08-0.34 nmol/kg/day).

Example 4: A Randomized, Double-Blinded, Multi-Center, Placebo Controlled Study to Evaluate the Efficacy and Safety of Recombinant Human Neuregulin 1 in Patients with Chronic Heart Failure Based on Standard Treatment To evaluate the efficacy and safety of recombinant human neuregulin-1 for injection on chronic congestive heart failure and to investigate the effective dosage range of recombinant human neuregulin-1 for injection for treating chronic congestive heart failure, the phase II, double-blinded, multi-center, placebo controlled, standard treatment based study (Protocol ID: ZS-01-206) was carried out in multiple clinical centers in China. Sixty four patients diagnosed as chronic heart failure originating from one or more factors including dilated cardiomyopathy, hypertension, viral myocarditis, myocardial infarction, and alcoholic cardiomyopathy, were enrolled and randomized into 4 groups.

Investigational Product:

Specification: Neucardin™, a 61-amino acid polypeptide comprising the EGF-like domain of Neuregulin-1 β2 isoform and having the amino acid sequence set forth in SEQ ID NO:1, with the molecular weight of 7054 Dal (1 µg=0.14 nmol). 250 µg (5000 EU)/vial (1 µg=20 EU).

Preparation: For injection.

Mode of administration: Intravenously drip.

Storage: in safe place, with limited access and protected from light, at 3-8° C.

Placebo:

Specification: Excipient for Neucardin™. 250n/vial and without active recombinant human neuregulin-1 protein.

Dosage Groups:

Sixty four patients with chronic heart failure (LVEF≤40%, NYHA class established on ACEI/ARA, beta blocker, diuretic or digoxin with stable doses of these medications for 1 month) were designed to be enrolled and randomized into 4 dosage groups with 16 patients in each group (refer to Table 13).

TABLE 13

Dosage groups and regimen

| | Dosage | | | |
|---|---|---|---|---|
| | 0 µg/kg/day | 0.3 µg/kg/day | 0.6 µg/kg/day | 1.2 µg/kg/day |
| Administration | Intravenous infusion | | | |
| Volume | 50 ml | | | |
| Course | 10 hours per day, for consecutive 10 days | | | |

Study Procedures
1) Screening and baseline:
Obtain the written informed consent form;
Demography;
Collect the medical history;
Vital signs (supine blood pressure, pulse, respiratory rate, temperature);
Physical examination;
Blood/Urine routine, blood biochemistry;
Blood coagulation test: APTT, PT;
NT-proBNP;
ECG;
NYHA classification;
Ultrasonic cardiogram;
Chest radiography;
MRI;
Tissue Doppler (breast, liver, gallbladder, kidney, adrenal gland, pancrease, spleen, ovary, uterus, prostate);
Urine pregnancy test (women of child-bearing age);
Dyspnea evaluation at rest stage;
Quality of life;
Six minute walking test;
Verify the inclusion/exclusion criteria;
Urine volume for 24 hours;
Record adverse events and serious adverse events;
Record concomitant medications.
2) $1^{st}$ to $10^{th}$ day of drug administration
Vital signs (supine blood pressure, pulse, respiratory rate, temperature);
ECG;
Study drug administration;
Urine volume for 24 hours;
Record adverse events and serious adverse events;
Record concomitant medications.
3) $11^{th}$-$13^{th}$ day of the study
Vital signs (supine blood pressure, pulse, respiratory rate, temperature);
Physical examination;
ECG;
Blood/Urine routine, blood biochemistry;
Blood coagulation test: APTT, PT;
NT-proBNP;
Urine pregnancy test (women of child-bearing age);
Quality of life;
Six minute walking test;
MRI;
NYHA classification;
Dyspnea evaluation at rest stage;
Urine volume for 24 hours;
Record adverse events and serious adverse events;
Record concomitant medications.
4) $30^{th}$ and $90^{th}$ day of the study
Vital signs (supine blood pressure, pulse, respiratory rate, temperature);
Physical examination;
Blood/Urine routine, blood biochemistry;
Blood coagulation test: APTT, PT;
NT-proBNP;
ECG;
Chest radiography;
Six minute walking test;
MRI;
NYHA classification;
Dyspnea evaluation at rest stage;
Quality of life;
Record adverse events and serious adverse events;
Record concomitant medications.

Results and Analysis

Forty patients completed the trial. The primary efficacy endpoint is heart function parameters (LVEF, LVEDV and LVESV) at day 30. Concerning LVEF, the mean value of LVEF is decreased from 21.54% at baseline to 20.93% at day 30 in the group of placebo. While in the group of 0.3 μg/kg/day, the mean value of LVEF is slightly improved from 25.08% at baseline to 26.61%, the percentage increase is 4.88%. And in the group of 0.6 μg/kg/day, the mean value of LVEF is significantly increased from 23.03% at baseline to 28.01% at day 30, the percentage increase is 27.11% (refer to Table 14).

Concerning LVEDV, the mean value of LVEDV is increased from 392.16 ml at baseline to 413.35 ml at day 30 in the group of placebo, with the percentage increase of 5.93%. While in the group of 0.3 μg/kg/day, the mean value of LVEDV slightly decreased from 333.62 ml at baseline to 323.22 ml at day 30, with the percentage decrease 3.28%. In the group of 0.6 μg/kg/day and 1.2n/kg/day, the mean value of LVEDV significantly decreased from 408.51 ml and 397.04 ml at baseline to 386.89 ml and 374.46 ml at day 30, respectively, both with the percentage decrease more than 5% (refer to Table 15).

TABLE 14

| | LVEF value before and after treatment | | | |
|---|---|---|---|---|
| | Group A (Placebo) n = 10 | Group B 0.3 μg/kg/day n = 11 | Group C 0.6 μg/kg/day n = 11 | Group D 1.2 μg/kg/day n = 8 |
| Baseline (%) | 21.54 ± 4.73 | 25.08 ± 7.64 | 23.03 ± 10.23 | 22.64 ± 4.24 |
| Day 30 (%) | 20.93 ± 8.53 | 26.61 ± 9.68 | 28.01 ± 11.27 | 22.01 ± 7.21 |
| ΔLVEF (%) | −0.61 ± 8.22 | 1.53 ± 3.81 | 4.98 ± 5.37 | −0.63 ± 4.34 |
| Changed percentage (%) | −1.39 ± 33.34 | 4.88 ± 17.07 | 27.11 ± 31.12 | −4.01 ± 19.42 |

TABLE 15

LVEDV value before and after treatment

| | Group A (Placebo) n = 10 | Group B 0.3 µg/kg/day n = 11 | Group C 0.6 µg/kg/day n = 11 | Group D 1.2 µg/kg/day n = 8 |
|---|---|---|---|---|
| Baseline (ml) | 392.16 ± 107.38 | 333.62 ± 106.14 | 408.51 ± 142.85 | 397.04 ± 86.94 |
| Day 30 (ml) | 413.35 ± 143.98 | 323.22 ± 111.86 | 386.89 ± 150.14 | 374.46 ± 84.47 |
| ΔLVEDV (ml) | 21.20 ± 108.13 | −10.40 ± 33.19 | −21.63 ± 42.72 | −22.58 ± 37.72 |
| Changed percentage (%) | 5.93 ± 31.48 | −3.28 ± 11.34 | −5.64 ± 10.03 | −5.41 ± 8.53 |

The result of LVESV is similar with that of LVEDV, in the group of placebo, the mean value of LVESV increased from 310.54 ml at baseline to 335.78 ml at day 30, with the percentage increase 9.45%. While in each group of recombinant neuregulin treatment, the mean value of LVESV decreased. For the group of 0.6 µg/kg/day as an example, the mean value of LVESV decreased from 325.02 ml at baseline to 291.71 ml at day 30, with the percentage decrease 11.58% (refer to Table 16).

TABLE 16

LVESV value before and after treatment

| | Group A (Placebo) n = 10 | Group B 0.3 µg/kg/day n = 11 | Group C 0.6 µg/kg/day n = 11 | Group D 1.2 µg/kg/day n = 8 |
|---|---|---|---|---|
| Baseline (ml) | 310.54 ± 97.54 | 254.85 ± 100.86 | 325.02 ± 142.70 | 308.46 ± 74.37 |
| Day 30 (ml) | 335.78 ± 145.37 | 244.01 ± 110.30 | 291.71 ± 147.66 | 292.22 ± 69.20 |
| ΔLVESV (ml) | 25.24 ± 119.19 | −10.84 ± 25.10 | −33.31 ± 44.54 | −16.24 ± 20.89 |
| Changed percentage (%) | 9.45 ± 48.04 | −5.33 ± 12.89 | −11.58 ± 12.74 | −5.01 ± 6.77 |

NT-proBNP is an important independent prognostic factor for survival rate of patients with chronic heart failure. From the result, the value of NT-proBNP in the group of placebo and 1.2 µg/kg/day at day 30 and day 90 increased significantly compared to that of baseline. While in the group of 0.3n/kg/day and 0.6 µg/kg/day, it shows a trend of decrease (refer to Table 17), suggesting a better prognosis.

TABLE 17

Change of NT-proBNP at day 30 and day 90

| | Group A (Placebo) n = 10 | Group B 0.3 µg/kg/day n = 11 | Group C 0.6 µg/kg/day n = 11 | Group D 1.2 µg/kg/day n = 8 |
|---|---|---|---|---|
| Baseline (fmol/ml) | 1013 ± 634.5 | 1732 ± 1638.4 | 1403 ± 1755.2 | 859 ± 460.7 |
| Day 30 (fmol/ml) | 811 ± 436.6 | 1631 ± 1222.1 | 1021 ± 1045.9 | 822 ± 349.4 |
| Changed Percentage (%) | 6.54 ± 74.29 | 25.68 ± 72.09 | −4.27 ± 41.37 | 49.42 ± 118.19 |
| Day 90 (fmol/ml) | 869 ± 440.9 | 1663 ± 1664.1 | 1112 ± 1418.5 | 847 ± 316.2 |
| Changed Percentage (%) | 26.79 ± 102.61 | −3.5 ± 60.07 | 8.66 ± 74.83 | 45.99 ± 97.45 |

There were adverse events in each group, particularly, in the group of 1.2 µg/kg/day, 100% patients in the group experienced at least on adverse event. The most commonly reported individual AEs were nausea, poor appetite and headache. There was no serious adverse events reported (refer to Table 18). Most reported adverse events relieved without treatment and the rest relieved after the cease of study drug administration or by symptomatic treatment and without sequelae.

There were no clinical significant abnormalities identified concerning to vital signs and physical examination.

From the results of efficacy and safety, we can find that in the dosage of 0.3-1.2 µg/kg/day (6-24 EU/kg/day or 0.04-0.17 nmol/kg/day), recombinant human neuregulin-1 is effective and safe for the treatment of chronic heart failure.

TABLE 18

Incidence of AE and SAE in each group

|  | Dosage group | With | Without | Incidence (%) |
|---|---|---|---|---|
| AE | Group A (n = 11) | 6 | 5 | 54.5 |
|  | Group B (n = 11) | 7 | 4 | 63.64 |
|  | Group C (n = 12) | 8 | 4 | 66.67 |
|  | Group D (n = 10) | 10 | 0 | 100 |
| SAE | Group A (n = 11) | 0 | 11 | 0 |
|  | Group B (n = 11) | 0 | 11 | 0 |
|  | Group C (n = 12) | 0 | 12 | 0 |
|  | Group D (n = 10) | 0 | 10 | 0 |

From the results of these clinical trials, we can make a conclusion that in the dosage of 0.3-2.4 μg/kg/day (6-48 EU/kg/day or 0.04-0.34 nmol/kg/day), recombinant human neuregulin-1 is tolerant and effective for the treatment of chronic heart failure.

What is claimed is:

1. A method for treating heart failure in a mammal in need thereof, which method comprises administering to the mammal in need thereof a neuregulin 1 protein in an amount:
   a) from about 0.3 μg to about 2.4 μg/kg/day;
   b) from about 6 EU to about 48 EU/kg/day; or
   c) from about 0.04 nmol to about 0.34 nmol/kg/day,
   whereby heart function of the mammal with the heart failure is improved.

2. The method of claim 1, wherein the neuregulin 1 protein is neuregulin 1 β2 isoform.

3. The method of claim 1, wherein the neuregulin 1 protein comprises the amino acid sequence set forth in SEQ ID NO:1.

4. The method of claim 1, wherein the neuregulin 1 protein consists of the amino acid sequence set forth in SEQ ID NO:1.

5. The method of claim 1, wherein the neuregulin 1 protein is administered to the mammal intravenously.

6. The method of claim 1, wherein the neuregulin 1 protein is administered to the mammal for one day or multiple days.

7. The method of claim 6, wherein the neuregulin 1 protein is administered to the mammal for at least 10 days.

8. The method of claim 7, wherein the neuregulin 1 protein is administered to the mammal for from 10 minutes to 12 hours per day.

9. The method of claim 8, wherein the neuregulin 1 protein is administered to the mammal 10 hours per day for 10 days.

10. The method of claim 1, wherein the mammal has or is suspected of having heart failure.

11. The method of claim 10, wherein the heart failure is caused by one or more ischaemic, congenital, rheumatic, idiopathic, viral or toxic factors.

12. The method of claim 1, where in the mammal is human.

* * * * *

SEQUENCE LISTING

```
<160> NUMBER OF SEQ ID NOS: 2

<210> SEQ ID NO 1
<211> LENGTH: 61
<212> TYPE: PRT
<213> ORGANISM: Homo sapiens

<400> SEQUENCE: 1

Ser His Leu Val Lys Cys Ala Glu Lys Glu Lys Thr Phe Cys Val Asn
1               5                  10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu Glu Leu Tyr Gln
    50                  55                  60

<210> SEQ ID NO 2
<211> LENGTH: 23
<212> TYPE: PRT
<213> ORGANISM: Homo sapiens

<400> SEQUENCE: 2

Ala Glu Lys Glu Lys Thr Phe Cys Val Asn Gly Gly Glu Cys Phe Met
1               5                  10                  15

Val Lys Asp Leu Ser Asn Pro
            20
```